US012214270B2

(12) United States Patent
Xu et al.

(10) Patent No.: US 12,214,270 B2
(45) Date of Patent: Feb. 4, 2025

(54) MOTION DATA MONITORING METHOD AND APPARATUS

(71) Applicant: Honor Device Co., Ltd., Shenzhen (CN)

(72) Inventors: Teng Xu, Shenzhen (CN); Xiaohan Chen, Shenzhen (CN); Bin Yang, Shenzhen (CN); Yue Li, Shenzhen (CN)

(73) Assignee: Honor Device Co., Ltd., Shenzhen (CN)

( * ) Notice: Subject to any disclaimer, the term of this patent is extended or adjusted under 35 U.S.C. 154(b) by 300 days.

(21) Appl. No.: 17/624,171

(22) PCT Filed: Jul. 3, 2020

(86) PCT No.: PCT/CN2020/100223
§ 371 (c)(1),
(2) Date: Dec. 30, 2021

(87) PCT Pub. No.: WO2021/004398
PCT Pub. Date: Jan. 14, 2021

(65) Prior Publication Data
US 2022/0362654 A1  Nov. 17, 2022

(30) Foreign Application Priority Data
Jul. 5, 2019  (CN) .......................... 201910604486.2

(51) Int. Cl.
*A63B 71/06* (2006.01)
*G01C 19/00* (2013.01)
(Continued)

(52) U.S. Cl.
CPC .......... *A63B 71/0619* (2013.01); *G01C 19/00* (2013.01); *G01P 13/00* (2013.01);
(Continued)

(58) Field of Classification Search
CPC ........ A63B 71/0619; A63B 2071/0661; A63B 2220/34; A63B 2220/40; A63B 2220/836;
(Continued)

(56) References Cited

U.S. PATENT DOCUMENTS 6,836,744 B1   12/2004  Asphahani et al.
7,949,487 B2    5/2011  Sugihara et al.
(Continued)

FOREIGN PATENT DOCUMENTS

CN      101232979 A      7/2008
CN      106127135 A     11/2016
(Continued)

OTHER PUBLICATIONS

Guo, "Pedestrian Positioning Method Based on MIMU under Random Gaits," Electronic Technology & Information Science, Jun. 2018, pp. 26-28 (with English translation) (12 total pages).
(Continued)

*Primary Examiner* — Suman K Nath
(74) *Attorney, Agent, or Firm* — Rimon PC

(57) ABSTRACT

The motion data monitoring method includes: collecting, by an electronic device, an angular velocity signal and an acceleration signal of a user; obtaining, by the electronic device, a waveform feature of the angular velocity signal based on the angular velocity signal, and obtaining a waveform feature of the acceleration signal based on the acceleration signal; determining, by the electronic device, a gait feature of the user according to the waveform feature of the angular velocity signal and the waveform feature of the acceleration signal, where the gait feature includes a duration of flight from off-ground of a foot of the user to touching of the ground; and determining, by the electronic device, motion data according to the gait feature, where the motion data includes a jump height.

11 Claims, 9 Drawing Sheets

(51) Int. Cl.
G01P 13/00 (2006.01)
G01P 15/18 (2013.01)
(52) U.S. Cl.
CPC ...... *G01P 15/18* (2013.01); *A63B 2071/0661* (2013.01); *A63B 2220/34* (2013.01); *A63B 2220/40* (2013.01); *A63B 2220/836* (2013.01); *A63B 2225/50* (2013.01)
(58) Field of Classification Search
CPC . A63B 2225/50; A63B 71/06; A63B 2230/62; G01C 19/00; G01C 22/006; G01P 13/00; G01P 15/18; A61B 5/742; A61B 5/112; A61B 5/1122; A61B 5/1123; A61B 5/681; A61B 5/7264; A61B 2503/10; A61B 2505/09; A61B 2562/0219
See application file for complete search history.

(56) References Cited

U.S. PATENT DOCUMENTS

| | | | |
|---|---|---|---|
| 2009/0063088 A1 | 3/2009 | Chen | |
| 2014/0074179 A1* | 3/2014 | Heldman | A61B 5/1101 607/45 |
| 2015/0057966 A1 | 2/2015 | Winter et al. | |
| 2015/0276793 A1* | 10/2015 | Takenaka | A61B 5/1121 73/504.03 |
| 2015/0293143 A1 | 10/2015 | Zao et al. | |

FOREIGN PATENT DOCUMENTS

| | | |
|---|---|---|
| CN | 106730771 A | 5/2017 |
| CN | 106778694 A | 5/2017 |
| CN | 104729507 B | 1/2018 |
| CN | 108634960 A | 10/2018 |
| CN | 109260647 A | 1/2019 |
| JP | 5586050 B2 | 9/2014 |
| WO | 2007015134 A2 | 2/2007 |
| WO | 2012152420 A1 | 11/2012 |

OTHER PUBLICATIONS

Bojan Milosevic et al. "Wearable Inertial Sensor for Jump Performance Analysis," WearSys '15: Proceedings of the 2015 workshop on Wearable Systems and Applications, May 2015, pp. 15-20.

M. R. Garcia, et al. "Portable measurement system of vertical jump using an Inertial Measurement Unit and pressure sensors," 2016 XXI Symposium on Signal Processing, Images and Artificial Vision (STSIVA), 2016, pp. 1-5.

Y. Ibata, et al. "Measurement of three-dimensional posture and trajectory of lower body during standing long jumping utilizing body-mounted sensors," 2013 34th Annual International Conference of the IEEE Engineering in Medicine and Biology Society (EMBC), 2013, pp. 4891-4894.

\* cited by examiner

Electronic device

501. The electronic device collects an angular velocity signal and an acceleration signal of a user 502. The electronic device obtains a waveform feature of the angular velocity signal based on the angular velocity signal, and obtains a waveform feature of the acceleration signal based on the acceleration signal 503. The electronic device determines a gait feature of the user according to the waveform feature of the angular velocity signal and the waveform feature of the acceleration signal, where the gait feature of the user includes a duration of flight from off-ground of a foot of the user to touching of the ground 504. The electronic device determines motion data according to the gait feature 505. The electronic device performs action classification according to the waveform feature of the angular velocity signal, the waveform feature of the acceleration signal, and the motion data, where an action classification result includes at least one of vertical jump, running jump, and sideward movement 506. The electronic device performs template matching on the motion data and database data, and outputs a character classification and/or a person tag of the user

FIG. 5

Vertical jump    Sideward movement    Running jump

MOTION DATA MONITORING METHOD AND APPARATUS

CROSS-REFERENCE TO RELATED APPLICATIONS

This application is a US national stage application of International Application No. PCT/CN2020/100223, filed on Jul. 3, 2020, which claims priority to Chinese Patent application Ser. No. 201910604486.2, filed with the China National Intellectual Property Administration on Jul. 5, 2019. Both of them are hereby incorporated by reference in its entirety.

TECHNICAL FIELD

This application relates to the field of terminals, and in particular, to a motion data monitoring method and apparatus.

BACKGROUND

With continuous development of communication technologies, increasing electronic devices (such as a wearable device (WD)) entered our field of vision. The wearable device is a portable device that may be directly worn on a body or integrated into clothes or accessories of a user.

One function of the wearable device is to record a motion process of a user. For example, wearable devices such as an energy bracelet or pedometer shoes may be configured to record parameters such as a quantity of movement steps, a distance, and calories burned during running.

Sports involving more diversified actions, such as basketball, volleyball, and parkour, may include actions such as walking, trotting, jumping, and sideward movement. However, current smart wearable devices cannot monitor features of the actions desirably, failing to provide more desirable sports experience for users.

SUMMARY

Embodiments of this application provide motion data monitoring, for use in monitoring motion data of a user in sports (for example, basketball) involving diversified actions in real time, and improving the user experience in sports.

According to a first aspect, an embodiment of this application provides a motion data monitoring method. The method includes: collecting, by an electronic device, an angular velocity signal and an acceleration signal of a user; obtaining, by the electronic device, a waveform feature of the angular velocity signal based on the angular velocity signal, and obtaining a waveform feature of the acceleration signal based on the acceleration signal; determining, by the electronic device, a gait feature of the user according to the waveform feature of the angular velocity signal and the waveform feature of the acceleration signal, where the gait feature includes a duration of flight from off-ground of a foot of the user to touching of the ground; and determining, by the electronic device, motion data according to the gait feature, where the motion data includes a jump height.

Based on the motion data monitoring method provided in this application, the electronic device may collect the angular velocity signal and the acceleration signal of the user and process the angular velocity signal and the acceleration signal to obtain the motion data of the user. The angular velocity signal and the acceleration signal of the user may be collected by using a six-axis sensor. Costs are low and temporally synchronous transmission and data fusion for a plurality of sensor units are not required. Motion data (such as a jump height) of the user in diversified sports (for example, basketball) can be monitored in real time, and the user experience in sports can be improved.

In a possible implementation, the collecting, by an electronic device, an angular velocity signal and an acceleration signal of a user includes: collecting, by the electronic device, an angular velocity signal and an acceleration signal of the foot or a leg of the user. The foot of the user includes parts such as an instep and a sole of the user. The leg of the user includes parts such as an ankle, a calf, a knee, and a thigh of the user.

In a possible implementation, the determining, by the electronic device, motion data according to the gait feature includes: determining, by the electronic device, a first component of the jump height according to the duration of flight; determining, by the electronic device, a second component of the jump height according to an integration of the acceleration signal over the duration of flight; and determining, by the electronic device, the jump height according to the first component and the second component. In this embodiment of this application, the jump height is determined by using the duration of flight and the integration of the acceleration signal over the duration of flight, so that accuracy of the jump height can be improved.

In a possible implementation, the determining, by the electronic device, a first component of the jump height according to the duration of flight includes:

$$H_t = \frac{1}{2} * g \left(\frac{\Delta t}{2}\right)^2,$$

where $H_t$ represents the first component, $\Delta t$ represents the duration of flight, and g represents an acceleration of gravity; the determining, by the electronic device, a second component of the jump height according to an integration of an acceleration over the duration of flight includes: $H_a = \iint_{t^0 + \Delta t}^{t^0} (k * acc_z) dt$, where $H_a$ represents the second component, $\Delta t$ represents the duration of flight, $t^0$ represents an initial moment of the duration of flight, k is a correction parameter, and $acc_z$ represents a signal component of an acceleration of the user in the z-axis direction of a local horizontal coordinate system; and the determining, by the electronic device, the jump height according to the first component and the second component includes: when $|H_a - H_t| < \Delta H$, $H = \frac{1}{2} * (H_a + H_t)$, where a threshold $\Delta H$ is a preset threshold, and H is the jump height.

In a possible implementation, the determining, by the electronic device, a gait feature of the user according to the waveform feature of the angular velocity signal and the waveform feature of the acceleration signal includes: determining, by the electronic device, the gait feature of the user according to the waveform feature of the angular velocity signal, the waveform feature of the acceleration signal, and an attitude angle matrix, where the attitude angle matrix is determined according to the angular velocity signal and the acceleration signal. The attitude angle matrix includes an angle of a carrier coordinate system of the electronic device relative to the local horizontal coordinate system over a period of time, and may be used to represent an attitude feature of the user. Therefore, when an action of the user changes relatively intricately or quickly, the action of the user may be further recognized according to the attitude angle matrix. In this way, the motion data can be determined more accurately.

In a possible implementation, the method further includes: constructing, by the electronic device, an attitude angle correction matrix according to a preset condition, where the preset condition includes presetting a velocity of the foot of the user before the off-ground to 0 and a displacement in a vertical direction to 0, and presetting a velocity of the foot of the user after the touching of the ground to 0 and a displacement in the vertical direction to 0; and correcting, by the electronic device, the attitude angle matrix according to the attitude angle correction matrix. In this way, a temperature drift and a time drift as a result of a gyroscope sensor and an acceleration sensor can be effectively eliminated.

In a possible implementation, the correcting, by the electronic device, the attitude angle matrix according to the attitude angle correction matrix includes:

$$R_c = C * R, \text{ where}$$

$$C = \begin{bmatrix} 1 & 0 & 0 \\ 0 & \cos\gamma & \sin\gamma \\ 0 & -\sin\gamma & \cos\gamma \end{bmatrix} \begin{bmatrix} \cos\beta & 0 & -\sin\beta \\ 0 & 1 & 0 \\ \sin\beta & 0 & \cos\beta \end{bmatrix} \begin{bmatrix} \cos\alpha & -\sin\alpha & 0 \\ \sin\alpha & \cos\alpha & 0 \\ 0 & 0 & 1 \end{bmatrix};$$

$$\gamma = \gamma_1 + \gamma_2, \gamma_1 = \arctan\left(\frac{v_z}{g\Delta t}\right), \gamma_2 = \arctan\left(\frac{H_z}{S}\right);$$

$$\beta = \arctan\left(\frac{v_y}{g\Delta t}\right), \text{ and } \alpha = \arctan\left(\frac{v_x}{g\Delta t}\right),$$

where

C represents the attitude angle correction matrix, R represents the attitude angle matrix, $R_c$ represents a corrected attitude angle matrix, α, β, and γ are respectively rotation angles in an x-axis direction, a y-axis direction, and the z-axis direction in the local horizontal coordinate system, $v_x$, $v_y$, and $v_z$ are respectively velocity components in the x-axis direction, the y-axis direction, and the z-axis direction, $H_z$ is a displacement in the z-axis direction, S is a displacement of the foot of the user after the off-ground and before the touching of the ground, and Δt is a time interval from the off-ground of the foot of the user to the touching of the ground.

In a possible implementation, the motion data further includes at least one of a movement distance, a quantity of steps, and a movement velocity of the user. The motion data may further include a heartbeat, a body temperature, a calorie consumption, and the like of the user. This is not limited in this application.

In a possible implementation, the method further includes: performing, by the electronic device, zero-velocity correction according to a local minimum value time point of a movement velocity in a time interval from the touching of the ground to the off-ground; and/or performing, by the electronic device, distance correction according to a local minimum value time point of a displacement in the vertical direction in the time interval from the touching of the ground to the off-ground. In this way, a temperature drift and a time drift as a result of a gyroscope sensor and an acceleration sensor can be effectively eliminated.

In a possible implementation, the method further includes: performing, by the electronic device, action classification according to the waveform feature of the angular velocity signal, the waveform feature of the acceleration signal, and the motion data, where an action classification result includes at least one of vertical jump, running jump, and sideward movement. In this way, the user can learn a clearer motion status of the user based on the action classification result, so that the user experience can be improved.

In a possible implementation, the method further includes: performing, by the electronic device, template matching on the motion data and database data, and outputting a character classification and/or a person tag of the user. This enhances enjoyment of sports for the user and can improve the user experience.

According to a second aspect, an embodiment of this application provides an electronic device. The electronic device includes: a collection unit, configured to collect an angular velocity signal and an acceleration signal of a user; an obtaining unit, configured to obtain a waveform feature of the angular velocity signal based on the angular velocity signal, and obtain a waveform feature of the acceleration signal based on the acceleration signal; and a determining unit, configured to determine a gait feature of the user according to the waveform feature of the angular velocity signal and the waveform feature of the acceleration signal, where the gait feature includes a duration of flight from off-ground of a foot of the user to touching of the ground; and the determining unit is further configured to determine motion data according to the gait feature, and the motion data includes a jump height.

In a possible implementation, the collection unit is configured to collect an angular velocity signal and an acceleration signal of the foot or a leg of the user.

In a possible implementation, the determining unit is configured to: determine a first component of the jump height according to the duration of flight; determine a second component of the jump height according to an integration of the acceleration signal over the duration of flight; and determine the jump height according to the first component and the second component.

In a possible implementation, $$H_t = \frac{1}{2} * g \left(\frac{\Delta t}{2}\right)^2,$$

where $H_t$ represents the first component, Δt represents the duration of flight, and g represents an acceleration of gravity; $H_a = \iint_{t^0+\Delta t}^{t^0} (k * acc_z) dt$, where $H_a$ represents the second component, Δt represents the duration of flight, $t^0$ represents an initial moment of the duration of flight, k is a correction parameter, and $acc_z$ represents a signal component of an acceleration of the user in a z-axis direction of a local horizontal coordinate system; and when $|H_a - H_t| < \Delta H$, $H = \frac{1}{2} * (H_a + H_t)$, where a threshold ΔH is a preset threshold, and H is the jump height.

In a possible implementation, the determining unit is configured to determine the gait feature of the user according to the waveform feature of the angular velocity signal, the waveform feature of the acceleration signal, and an attitude angle matrix, where the attitude angle matrix is determined according to the angular velocity signal and the acceleration signal.

In a possible implementation, the determining unit is further configured to: construct an attitude angle correction matrix according to a preset condition, where the preset condition includes presetting a velocity of the foot of the user before the off-ground to 0 and a displacement in a vertical direction to 0, and presetting a velocity of the foot of the user after the touching of the ground to 0 and a displacement in the vertical direction to 0; and correct the attitude angle matrix according to the attitude angle correction matrix.

In a possible implementation, $R_c=C*R$, where $$C = \begin{bmatrix} 1 & 0 & 0 \\ 0 & \cos\gamma & \sin\gamma \\ 0 & -\sin\gamma & \cos\gamma \end{bmatrix} \begin{bmatrix} \cos\beta & 0 & -\sin\beta \\ 0 & 1 & 0 \\ \sin\beta & 0 & \cos\beta \end{bmatrix} \begin{bmatrix} \cos\alpha & -\sin\alpha & 0 \\ \sin\alpha & \cos\alpha & 0 \\ 0 & 0 & 1 \end{bmatrix};$$

$$\gamma = \gamma_1 + \gamma_2, \gamma_1 = \arctan\left(\frac{v_z}{g\Delta t}\right), \gamma_2 = \arctan\left(\frac{H_z}{S}\right);$$

$$\beta = \arctan\left(\frac{v_y}{g\Delta t}\right), \text{ and } \alpha = \arctan\left(\frac{v_x}{g\Delta t}\right),$$

where

C represents the attitude angle correction matrix, R represents the attitude angle matrix, $R_c$ represents a corrected attitude angle matrix, α, β, and γ are respectively rotation angles in an x-axis direction, a y-axis direction, and the z-axis direction in the local horizontal coordinate system, $v_x$, $v_y$, and $v_z$ are respectively velocity components in the x-axis direction, the y-axis direction, and the z-axis direction, $H_z$ is a displacement in the z-axis direction, S is a displacement of the foot of the user after the off-ground and before the touching of the ground, and Δt is a time interval from the off-ground of the foot of the user to the touching of the ground.

In a possible implementation, the motion data further includes at least one of a movement distance, a quantity of steps, and a movement velocity of the user.

In a possible implementation, the determining unit is further configured to: perform zero-velocity correction according to a local minimum value time point of a movement velocity in a time interval from the touching of the ground to the off-ground; and/or perform distance correction according to a local minimum value time point of a displacement in the vertical direction in the time interval from the touching of the ground to the off-ground.

In a possible implementation, the determining unit is further configured to perform action classification according to the waveform feature of the angular velocity signal, the waveform feature of the acceleration signal, and the motion data, where an action classification result includes at least one of vertical jump, running jump, and sideward movement.

In a possible implementation, the determining unit is further configured to perform template matching on the motion data and database data, and output a character classification and/or a person tag of the user.

For technical effects of the second aspect and the various possible implementations of the second aspect, refer to the technical effects of the first aspect and the various possible implementations of the first aspect. Details are not described herein again.

According to a third aspect, an embodiment of this application provides a computer readable storage medium including instructions, where the instructions, when run on a computer, cause the computer to perform any one of the methods provided in the first aspect.

According to a fourth aspect, an embodiment of this application provides a computer program product including instructions, where the instructions, when run on a computer, cause the computer to perform any one of the methods provided in the first aspect.

According to a fifth aspect, an embodiment of this application provides a chip system. The chip system includes a processor and may further include a memory. The chip system is configured to perform any one of the methods provided in the first aspect. The chip system may include chips, or may include chips and other discrete devices.

According to a sixth aspect, an embodiment of this application further provides an apparatus. The apparatus may be a processing device, an electronic device, or a chip. The apparatus includes a processor configured to perform any one of the methods provided in the first aspect. The apparatus may further include a memory configured to store program instructions and data. The memory may be a memory integrated in the apparatus or an off-chip memory disposed outside the apparatus. The memory is coupled to the processor. The processor may invoke and execute the program instructions stored in the memory to implement any one of the methods provided in the first aspect. The apparatus may further include a communication interface. The communication interface is used for the apparatus to communicate with other devices.

BRIEF DESCRIPTION OF DRAWINGS

FIG. 5 is a schematic flowchart of a method applicable to motion data monitoring according to an embodiment of this application;

DESCRIPTION OF EMBODIMENTS

Technical solutions in embodiments of this application are described below with reference to the accompanying drawings in the embodiments of this application. In the descriptions of this application, unless otherwise stated, "at least one" refers to one or more, and "a plurality of" refers to two or more. In addition, to facilitate clear description of the technical solutions in the embodiments of this application, words such as "first" and "second" are used in the embodiments of this application to distinguish the same objects or similar objects whose functions and purposes are basically the same. A person skilled in the art may understand that the words such as "first" and "second" do not restrict a quantity and an implementation sequence, and the terms such as "first" and "second" do not indicate a definite difference.

The embodiments of this application provide a motion data monitoring method. The method is applied to motion data monitoring scenarios for various sports such as basketball, volleyball, badminton, long jump, high jump, hurdles, and parkour. Motion data may include a duration of flight, a jump height, a quantity of jumps, a movement distance, a quantity of steps, a movement velocity, and the like.

Figure 1:
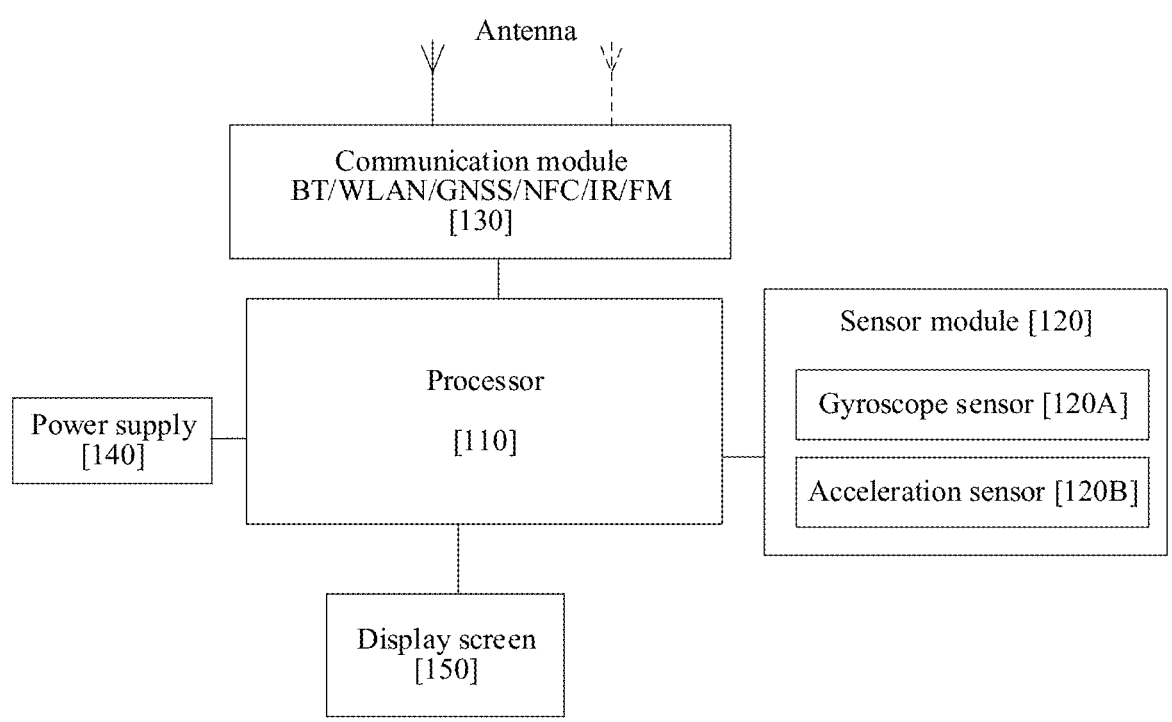
FIG. 1 is a schematic structural diagram of an electronic device according to an embodiment of this application.

FIG. 1 is a schematic structural diagram of an electronic device according to an embodiment of this application. The electronic device may be specifically a smart foot ring 100. The smart foot ring 100 may include a processor 110, a sensor module 120, a communication module 130, a power supply 140, a display screen 150, and the like. The sensor module may include a gyroscope sensor 120A, an acceleration sensor 120B, and the like.

A structure shown in the embodiments of the present invention constitutes no limitation on the smart foot ring 100. The smart foot ring may include more or fewer components than those shown in the figure, or some components may be combined, or some components may be split, or a different component deployment may be used. The components shown in the figure may be implemented by hardware, software, or a combination of software and hardware.

The processor 110 may include one or more processing units. For example, the processor 110 may include an application processor (application processor, AP), a modem processor, a graphics processing unit (graphics processing unit, GPU), an image signal processor (image signal processor, ISP), a controller, a memory, a video codec, a digital signal processor (digital signal processor, DSP), a baseband processor, and/or a neural-network processing unit (neural-network processing unit, NPU). Different processing units may be independent components, or may be integrated into the same processor.

The controller may be a decision maker who directs various components of the smart foot ring 100 to work in coordination according to instructions. The controller is a neural center and command center of the smart foot ring 100. The controller generates an operation control signal according to an instruction operation code and a timing signal, and completes control of obtaining and execution of the instructions.

A memory may be further disposed in the processor 110 to store instructions and data. In some embodiments, the memory in the processor is a cache memory. The memory may store instructions or data just used or reused by the processor. If the processor needs to use the instructions or the data again, the processor may directly invoke the instructions or the data from the memory. repeated access is avoided, and a waiting time is reduced for the processor, thereby improving system efficiency.

Figure 2:
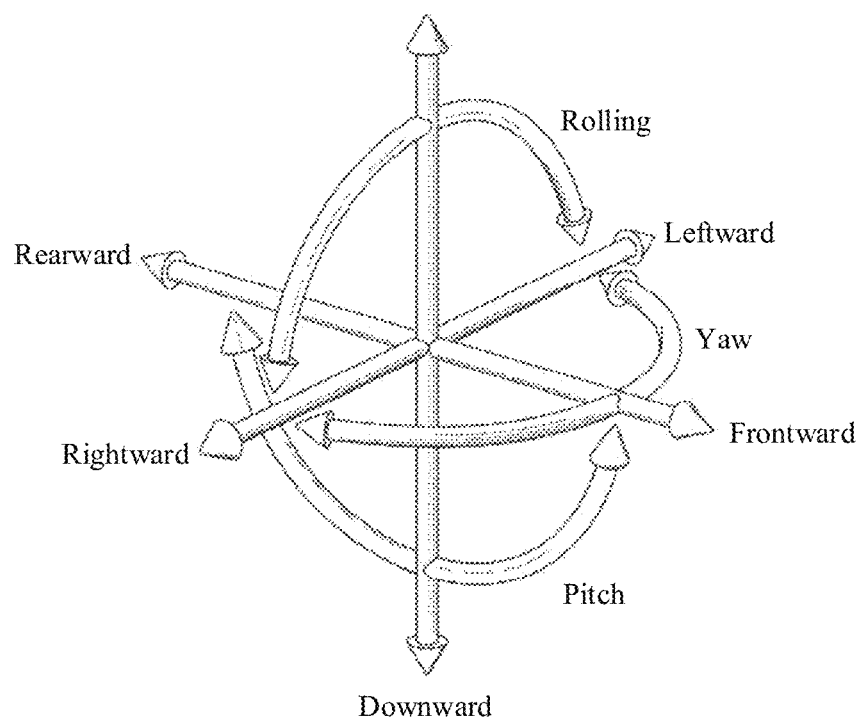
FIG. 2 is a schematic diagram of a roll angle, a pitch angle, and a yaw angle according to an embodiment of this application.

The gyroscope sensor 120A may be configured to determine a motion attitude of the smart foot ring 100. In some embodiments, the gyroscope sensor may be configured to determine angular velocities of the smart foot ring 100 along three axes (that is, an x-axis, a y-axis, and a z-axis) of a local horizontal coordinate system. Therefore, the gyroscope sensor may also be referred to as a three-axis gyroscope. As shown in FIG. 2, the gyroscope sensor can sense all-round dynamic information such as upward and downward tilting, forward and backward tilting, and leftward and rightward tilting. An attitude angle of the smart foot ring means an included angle between a carrier coordinate system and the local horizontal coordinate system. The attitude angle may be represented by using three angles: a roll angle, a pitch angle, and a yaw angle. The gyroscope sensor may be used for anti-shake for photographing. For example, when a shutter is pressed, the gyroscope sensor monitors a shake angle of the smart foot ring 100, and calculates, based on the angle, a distance that needs to be compensated for by a lens module. Therefore, a lens may be moved reversely to counteract the shake of the smart foot ring 100, thereby achieving anti-shake. The gyroscope sensor may be further used for navigation and a somatosensory game scenario.

Figure 3:
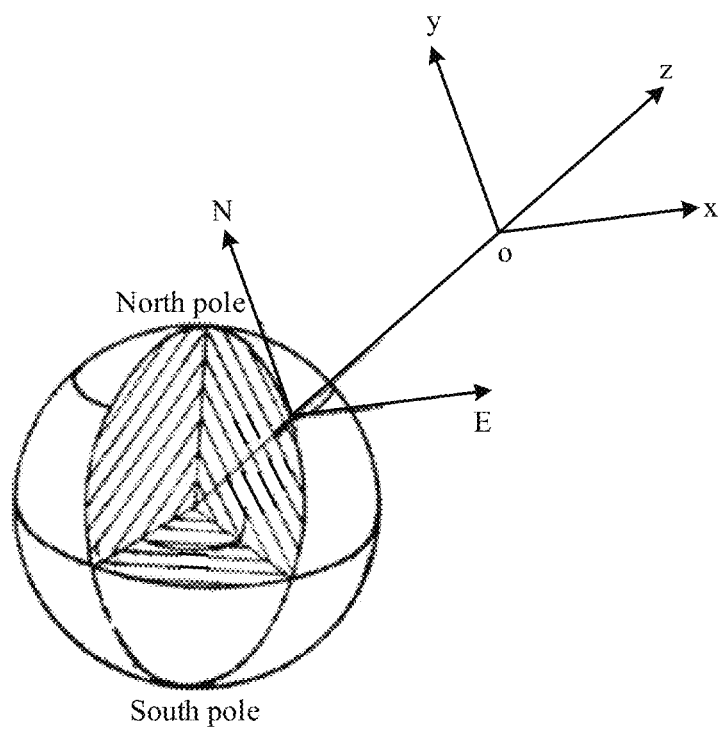
FIG. 3 is a schematic diagram of a local horizontal coordinate system according to an embodiment of this application.

A coordinate system of the gyroscope sensor is the local horizontal coordinate system. As shown in FIG. 3, an origin O of the local horizontal coordinate system is located at a center of mass of a carrier (that is, a device including the gyroscope sensor, for example, an electronic device 100), the x-axis is directed to east (E) along a local latitude, the y-axis is directed to north (N) along a local meridian line, and the z-axis is perpendicular to a local horizontal plane, is directed upward along a local geographic vertical line, and forms a right-handed rectangular coordinate system with the x-axis and the y-axis. A plane formed by the x-axis and the y-axis is the local horizontal plane, and a plane formed by the y-axis and the z-axis is a local meridian plane. Therefore, it may be understood that the coordinate system of the gyroscope sensor is as follows. The gyroscope sensor is used as the origin O, an axis directed to east along the local latitude is used as the x-axis, an axis directed to north along the local meridian line is used as the y-axis, and an axis directed upward (that is, a direction opposite to the geographic vertical line) along the local geographic vertical line is used as the z-axis.

The acceleration sensor 120B can monitor accelerations of the smart foot ring 100 in all directions (that is, the x-axis, the y-axis, and the z-axis of the local horizontal coordinate system). The acceleration sensor may also be referred to as a three-axis accelerator. The acceleration sensor can monitor a magnitude and a direction of gravity when the smart foot ring 100 is stationary. The acceleration sensor may be further used for recognition of an attitude of a terminal, switching between a horizontal screen and a vertical screen, and applications such as a pedometer.

A combination of a three-axis accelerator and a three-axis gyroscope may be referred to as a six-axis sensor.

The communication module 130 may provide solutions of wireless communications applied to the smart foot ring 100, including a wireless local area network (wireless local area network, WLAN) (for example, a wireless fidelity (wireless fidelity, Wi-Fi)) and Bluetooth, a global navigation satellite system (global navigation satellite system, GNSS), frequency modulation (frequency modulation, FM), a near field communication (near field communication, NFC) technology, an infrared (infrared, IR) technology, and the like. The communication module 130 may be one or more components into which at least one communication processing module is integrated. The communication module receives an electromagnetic wave through an antenna, performs frequency modulation and filtering processing on the electromagnetic wave signal, and sends the processed signal to the processor. The communication module 130 may further receive a to-be-sent signal from the processor, perform frequency modulation and amplification on the signal, and convert the signal into an electromagnetic wave for radiation through the antenna.

A display function of the smart foot ring 100 is achieved by using a GPU, a display screen 150, an application processor, and the like. The GPU is a microprocessor for image processing, and is connected to the display screen and the application processor. The GPU is configured to perform mathematical and geometric calculations and graphics rendering. The processor 110 may include one or more GPUs configured to execute program instructions to generate or change display information.

The display screen 150 is configured to display an image, a video, and the like. The display screen includes a display panel. The display panel may be a liquid crystal display (liquid crystal display, LCD), an organic light-emitting diode (organic light-emitting diode, OLED), an active-matrix organic light emitting diode (active-matrix organic light emitting diode, AMOLED), a Miniled, a MicroLed, a Micro-oLed, quantum dot light emitting diodes (quantum dot light emitting diodes, QLED), or the like.

The power supply 140 is configured to supply power to the processor, the display screen, the communication module, and the like.

The smart foot ring 100 may further include an external memory, an audio module, a camera, an indicator (for example, an indicator light), and the like. This is not limited in this application.

Figure 4:
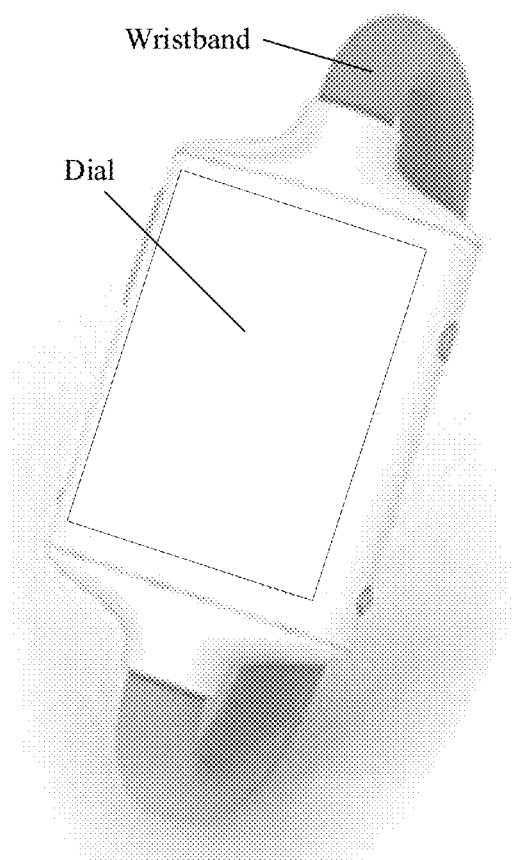
FIG. 4 is a schematic diagram of a product form of an electronic device according to an embodiment of this application.

FIG. 4 is a schematic diagram of a product form of an electronic device 100 according to an embodiment of this application. The electronic device may be specifically a smart foot ring 100. The smart foot ring 100 may include a wristband and a dial. The smart foot ring 100 may be worn on an ankle of a user by using the wristband, and display motion data, an action classification result, a character classification and/or a person tag, and the like by using a display screen of the dial.

Currently, a relatively general motion monitoring method for monitoring motion data of sports activities is to monitor spatial three-dimensional coordinates of target points distributed on a surface of a target based on an optical motion capture system, so as to monitor an action feature of the target. This solution requires to paste a large quantity of target points on the surface of the target before deployment for use, and requires model correction before use. A basic principle of this solution is a principle of computer vision imaging. This solution is achieved by using a set of precise and complex optical cameras. A plurality of high-velocity cameras track the target points distributed on the surface of the target from different angles to complete monitoring of action features of a whole body. The optical motion capture system is pretty cumbersome to install and operate, and costs relatively high. As a result, the optical motion capture system is difficult to promote and is not universal.

Another frequently used motion monitoring method is based on distributed sensors. This method is to collect parameters of all part nodes of a target based on distributed sensors on a surface of the target, perform time alignment on sensor data of all of the part nodes by using a time synchronization apparatus, transmit the parameters collected by the sensors at all of the nodes to a data processing unit by using a wireless protocol in real time for data fusion, and perform action recognition and classification according to a result outputted after the fusion. Before use of this monitoring method, presetting and temporally synchronous calibration are required for the sensor at each node on the surface of the target. A main disadvantage of this solution is that a plurality of displacement sensors are pasted on various parts of a body of an athlete. Therefore, costs are high, a large amount of preparatory work is required, temporally synchronous transmission is required for each sensor unit, data fusion is complex, and a data amount is large.

To resolve the problems, this application provides a motion data monitoring method. According to the method, an electronic device collects an angular velocity signal and an acceleration signal of a user and processes the angular velocity signal and the acceleration signal to obtain motion data of the user. The angular velocity signal and the acceleration signal of the user may be collected by using a six-axis sensor. Costs are low and temporally synchronous transmission and data fusion for a plurality of sensor units are not required. Motion data (such as a jump height) of the user in diversified sports (for example, basketball) can be monitored in real time, and the user experience in sports can be improved.

For ease of understanding, the following specifically describes a motion data monitoring method provided in an embodiment of this application with reference to accompanying drawings.

As shown in FIG. 5, an embodiment of this application provides a motion data monitoring method. The method includes the following steps.

501: An electronic device collects an angular velocity signal and an acceleration signal of a user.

The electronic device may obtain the acceleration signal of the user by using an acceleration sensor. The acceleration signal of the user includes values of accelerations along three coordinate axes of a local horizontal coordinate system sampled by the electronic device. The electronic device may obtain the angular velocity signal of the user by using a gyroscope. The angular velocity signal of the user includes values of angular velocities along the three coordinate axes of the local horizontal coordinate system sampled by the electronic device.

The electronic device may collect an angular velocity signal and an acceleration signal of a foot or a leg of the user. The foot of the user includes parts such as an instep and a sole of the user. The leg of the user includes parts such as an ankle, a calf, a knee, and a thigh of the user. For example, the electronic device may be integrated in a shoe sole, a shoe upper, or a shoe insole of the user to collect the angular velocity signal and the acceleration signal of the foot of the user. Alternatively, the electronic device may be a smart foot ring, and is worn on an ankle or a calf of the user to collect an angular velocity signal and an acceleration signal of the ankle or the calf of the user. Alternatively, the electronic device may be placed in a sports kneecap or a sports bandage to collect an angular velocity signal and an acceleration signal of the knee or the thigh of the user. That the electronic device collects the angular velocity signal and the acceleration signal of the foot of the user is used as an example below for description.

502: The electronic device obtains a waveform feature of the angular velocity signal based on the angular velocity signal, and obtains a waveform feature of the acceleration signal based on the acceleration signal.

The electronic device may extract the respective waveform features of the angular velocity signal and the acceleration signal based on the angular velocity signal collected by the gyroscope sensor and the acceleration signal collected by the acceleration sensor. The waveform features each include a quantity of crests, a quantity of troughs, a crest value, skewness, kurtosis, and the like.

503: The electronic device determines a gait feature of the user according to the waveform feature of the angular velocity signal and the waveform feature of the acceleration signal, where the gait feature of the user includes a duration of flight from off-ground of a foot of the user to touching of the ground.

It may be understood that a process of a sport performed by a human body may include a plurality of action cycles. One action cycle means a time taken for a complete action (for example, walking or jumping). One action cycle may include a series of typical gait changes. This typical gait change may be divided into different gait phases/periods. For example, one action cycle may also include an off-ground phase (also referred to as an off-ground period), a flight phase (also referred to as a flight period), and a ground-touching phase (also referred to as a ground-touching period). The off-ground phase may be a process from lifting of a heel to off-ground of a foot. The flight phase may be a process of movement of a foot in the air. The ground-touching phase may be a process in which a center of gravity shifts from a heel to a whole foot after the heel touches the ground until the whole foot touches the ground. An acceleration of the foot of the user gradually increases from an early stage to an end of the off-ground period. The acceleration of the foot of the user gradually decreases from an early stage to an end of the ground-touching period.

A motion process of one foot is used as an example. The foot may be considered to be in a stationary state during the off-ground period and the ground-touching period. In this case, a value in the gyroscope is close to zero, and a value in the acceleration sensor is approximately equal to an acceleration of gravity.

For example, it may be determined whether the user is in a stationary state based on a determining criterion $$\begin{cases} |\|acc\| - g| < acc_{thr} \\ \|gyro\| < gyro_{thr} \end{cases}, \text{ where } \|acc\| = \sqrt{acc_x^2 + acc_y^2 + acc_z^2},$$

$$\|gyro\| = \sqrt{gyro_x^2 + gyro_y^2 + gyro_z^2},$$

$acc_{thr}=1$ g, $gyro_{thr}=0.2$ rad/s, g is a unit of an acceleration of gravity, and 1 g is approximately equal to 9.8 m/s^2.

If it is determined that the user is in a stationary state, a gravity axis vector $$\vec{Z}_n = \frac{1}{n}\left(\sum_{k=1}^{i=n} acc_x, \sum_{k=1}^{i=n} acc_y, \sum_{k=1}^{i=n} acc_z\right)$$

of the electronic device (for example, a smart foot ring) may be obtained according to three-axis data of the acceleration sensor in a stationary state. If the user is in a motion state (a non-stationary state), a gravity axis of a previous step (that is, a last gravity axis calculated in the stationary state) may be reused.

Then, the gait feature of the user is determined based on the waveform feature of the angular velocity signal and the waveform feature of the acceleration signal, so as to achieve single-step splitting and obtain a duration of flight of each step. The single-step splitting means to split out each action cycle of a motion process over a period of time. For example, two adjacent crests in a waveform diagram in the acceleration sensor may represent one action cycle. An action corresponding to the action cycle may be a step of walking, a step of running, or a vertical jump. The gait feature of the user may further include a velocity at an off-ground time point, a velocity at a ground-touching time point, and the like. The off-ground time point is located at an end of the off-ground period, and the ground-touching time point is located at the early stage of the ground-touching period.

Figure 6:
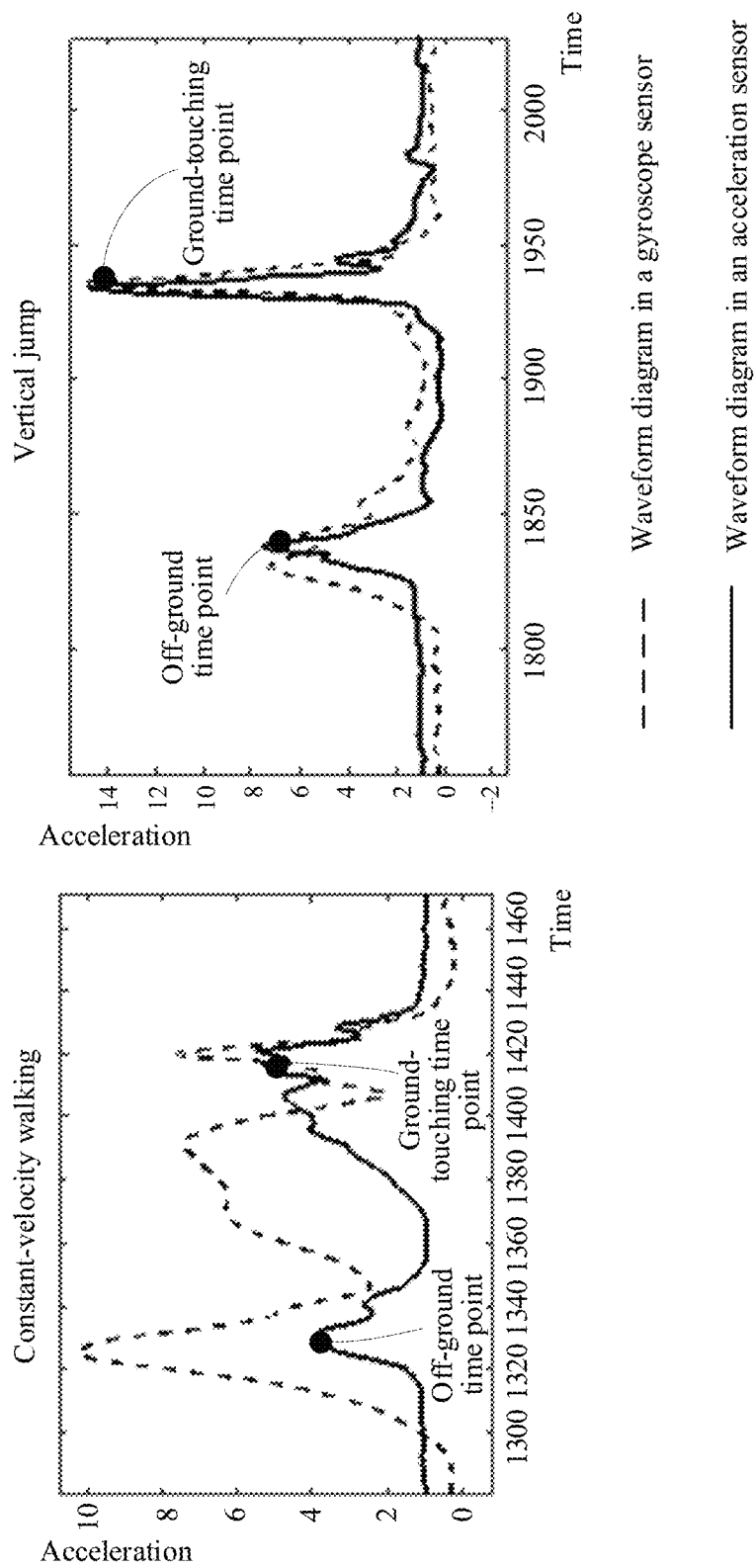
FIG. 6 is a schematic diagram of a waveform diagram in a gyroscope sensor and a waveform diagram in an acceleration sensor during constant-velocity walking and vertical jump according to an embodiment of this application.

FIG. 6 is a schematic diagram of a waveform diagram (a dashed-line part) in a gyroscope sensor and a waveform diagram (a solid-line part) in an acceleration sensor during constant-velocity walking and vertical jump (for example, perpendicular vertical jump). Constant-velocity walking and vertical jump may be distinguished from each other according to waveform features in the gyroscope sensor. During constant-velocity walking, an attitude of a foot changes in a flight state (that is, a state after off-ground and before ground-touching), and therefore a waveform in the gyroscope changes relatively greatly (having a relatively large quantity of crests). During vertical jump, an attitude of a foot changes little in a flight state, and therefore a waveform in the gyroscope changes little (having a relatively small quantity of crests). The off-ground time point (having a relatively small crest value) and the ground-touching time point (having a relatively large crest value) may be distinguished between each other according to waveform features in the acceleration sensor. Alternatively, the off-ground time point and the ground-touching time point may be distinguished between each other according to waveforms in the acceleration sensor and the gyroscope sensor. It may be learned from the waveform diagram in the acceleration sensor that, an off-ground acceleration (an acceleration corresponding to the off-ground time point) during constant-velocity walking is about 4 g, where g=9.8 m/s², a ground-touching acceleration (an acceleration corresponding to the ground-touching time point) is about 6 g, and a duration of flight is about 1420-1330=90 milliseconds. Each millisecond may be 5 ms, that is, the duration of flight is 450 ms. An off-ground acceleration during vertical jump is about 7 g, a ground-touching acceleration is about 14 g, and a duration of flight is about 1940-1840=100 milliseconds. That is, the duration of flight is 500 ms.

504: The electronic device determines motion data according to the gait feature.

The motion data may include at least one of a jump height (for example, a vertical jump height or a running jump height), a movement distance, a quantity of steps, and a movement velocity of the user in a sport. The motion data may further include a heartbeat, a body temperature, a calorie consumption, and the like of the user. This is not limited in this application.

For example, the motion data is a jump height. The electronic device may determine a first component of the jump height according to the duration of flight, determine a second component of the jump height according to an integration of the acceleration signal over the duration of flight, and determine the jump height according to the first component and the second component. In this embodiment of this application, the jump height is determined by using the duration of flight and the integration of the acceleration signal over the duration of flight, so that accuracy of the jump height can be improved.

For example, the determining, by the electronic device, a first component of the jump height according to the duration of flight includes:

$$H_t = \frac{1}{2} * g\left(\frac{\Delta t}{2}\right)^2,$$

where $H_t$ represents the first component, $\Delta t$ represents the duration of flight, and g represents an acceleration of gravity.

The determining, by the electronic device, a second component of the jump height according to an integration of an acceleration includes:

$H_a = \iint_{t^0 + \Delta t}^{t^p} (k * acc_z) dt$, where $H_a$ represents the second component, $\Delta t$ represents the duration of flight, $t^0$ represents an initial moment of the duration of flight, k is a correction parameter, and $acc_z$ represents a signal component of an acceleration of the user in a z-axis direction of a local horizontal coordinate system.

The determining, by the electronic device, the jump height according to the first component and the second component includes:

when $|H_a - H_t| < \Delta H$, $H = \frac{1}{2} * (H_a + H_t)$, where a threshold $\Delta H$ is a preset threshold, and H is the jump height.

In some embodiments, the electronic device may determine the motion data according to the gait feature and an attitude angle matrix, and the attitude angle matrix is determined according to the angular velocity signal and the acceleration signal. The attitude angle matrix includes an angle of a carrier coordinate system of the electronic device relative to the local horizontal coordinate system over a period of time, and may be used to represent an attitude feature of the user. Therefore, when an action of the user changes relatively intricately or quickly, the action of the user may be further recognized according to the attitude angle matrix. In this way, the motion data can be determined more accurately.

Optionally, the electronic device corrects the attitude angle matrix according to the attitude angle correction matrix. The electronic device may construct an attitude angle correction matrix according to a preset condition. The preset condition includes presetting a velocity of the foot of the user before the off-ground to 0 and a displacement in a vertical direction to 0, and presetting a velocity of the foot of the user after the touching of the ground to 0 and a displacement in the vertical direction to 0. An early off-ground time point may be an early period of the off-ground period (the off-ground phase), and post touching of the ground may be a later period of ground-touching period (the ground-touching phase). Based on a principle of linear compensation, the electronic device may correct all attitude angle matrices over a period from the off-ground of the foot to the touching of the ground. In this way, a temperature drift and a time drift as a result of the gyroscope sensor and the acceleration sensor can be effectively eliminated.

For example, $R_c = C * R$, where $$C = \begin{bmatrix} 1 & 0 & 0 \\ 0 & \cos\gamma & \sin\gamma \\ 0 & -\sin\gamma & \cos\gamma \end{bmatrix} \begin{bmatrix} \cos\beta & 0 & -\sin\beta \\ 0 & 1 & 0 \\ \sin\beta & 0 & \cos\beta \end{bmatrix} \begin{bmatrix} \cos\alpha & -\sin\alpha & 0 \\ \sin\alpha & \cos\alpha & 0 \\ 0 & 0 & 1 \end{bmatrix};$$

$\gamma = \gamma_1 + \gamma_2$, $\gamma_1 = \arctan\left(\frac{v_z}{g\Delta t}\right)$, $\gamma_2 = \arctan\left(\frac{H_z}{S}\right)$; $\beta = \arctan\left(\frac{v_y}{g\Delta t}\right)$; and $\alpha = \arctan\left(\frac{v_x}{g\Delta t}\right)$, where C represents the attitude angle correction matrix, R represents the attitude angle matrix, $R_c$ represents a corrected attitude angle matrix, $\alpha$, $\beta$, and $\gamma$ are respectively rotation angles in an x-axis direction, a y-axis direction, and the z-axis direction in the local horizontal coordinate system, $v_x$, $v_y$, and $v_z$ are respectively velocity components in the x-axis direction, the y-axis direction, and the z-axis direction, $H_z$ is a displacement in the z-axis direction, S is a displacement of the user after the off-ground and before the touching of the ground, and $\Delta t$ is a time interval from the off-ground of the user to the touching of the ground, that is, the duration of flight.

In this embodiment of this application, the attitude angle correction matrix is represented by using a direction cosine. The attitude angle correction matrix may also be represented based on an Euler angle or a quaternion value. This is not limited in this application.

Figure 7:
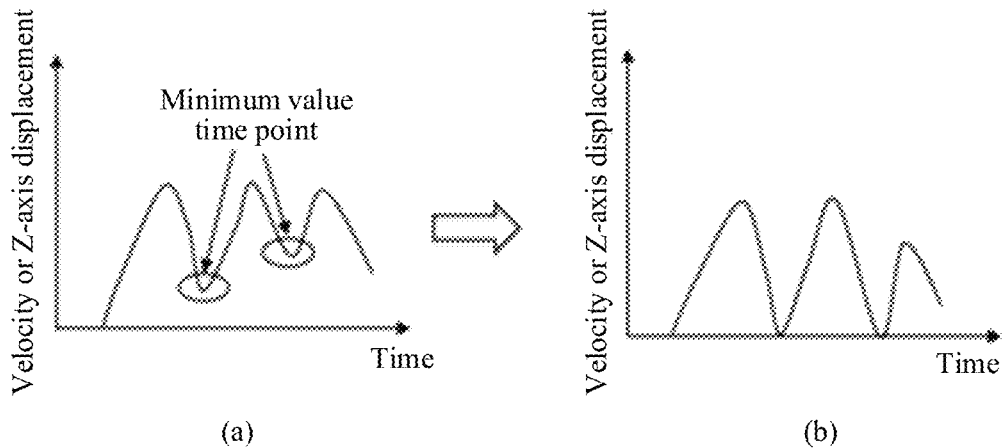
FIG. 7 is a schematic diagram of correcting a velocity or a Z-axis displacement according to an embodiment of this application.

In some embodiments, zero-velocity correction may be performed on a movement velocity of the foot in a time interval from the touching of the ground to the off-ground and a displacement in a vertical direction (that is, the Z axis) during motion. The time interval from the touching of the ground to the off-ground may include a ground-touching phase and an off-ground phase. As shown in (a) of FIG. 7, a local minimum value time point of a velocity/Z-axis displacement may be searched for in the time interval from the touching of the ground to the off-ground. A moment corresponding to the local minimum value time point is a zero velocity/zero displacement moment. As shown in (b) of FIG. 7, a movement velocity and a displacement at the moment corresponding to the local minimum value time point may be adjusted to zero to reduce a positioning error. In this way, a temperature drift and a time drift as a result of the gyroscope sensor and the acceleration sensor can be effectively eliminated.

That the electronic device is a smart foot ring is used as an example. It may be understood that, if the smart foot ring is worn on one foot of the user, the smart foot ring may determine motion data of the user based on an angular velocity signal and an acceleration signal of the foot. If smart foot rings are worn on both feet of the user, motion data of the user may be compared and corrected according to time stamps of motion data in the two foot rings, so as to obtain more accurate motion data.

505: The electronic device performs action classification according to the waveform feature of the angular velocity signal, the waveform feature of the acceleration signal, and the motion data, where an action classification result includes at least one of vertical jump, running jump, and sideward movement.

Figure 8:
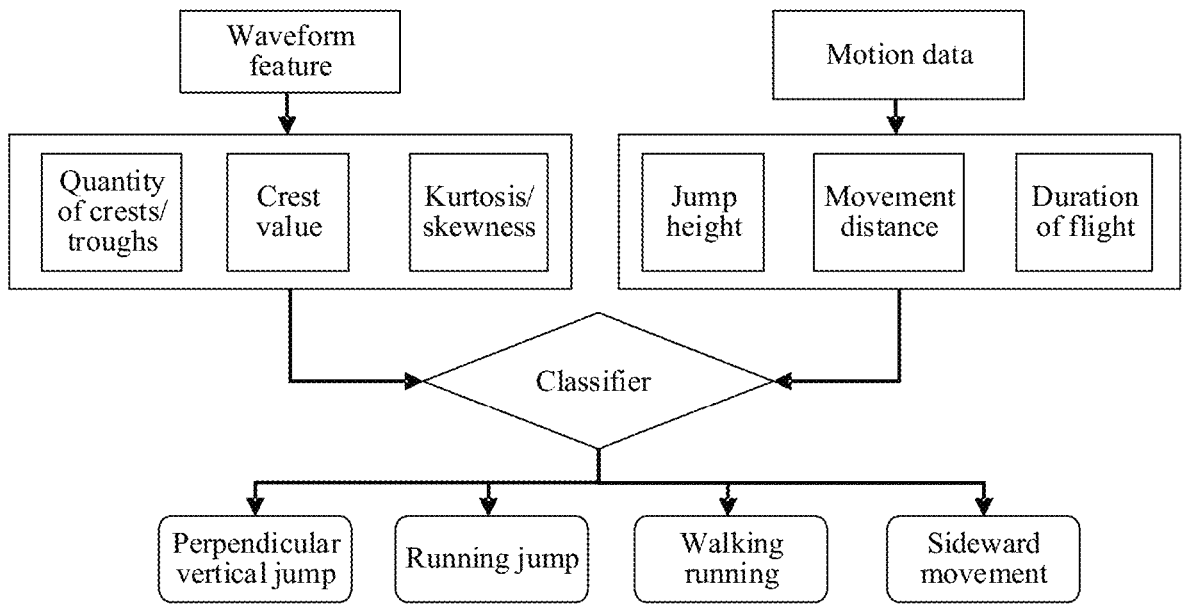
FIG. 8 is a schematic flowchart of classifying and recognizing action types by using a classifier based on respective waveform features and motion data of a gyroscope sensor and an acceleration sensor according to an embodiment of this application.

As shown in FIG. 8, action types may be classified and recognized by using a classifier based on respective waveform features and motion data of the gyroscope sensor and the acceleration sensor. Compared with action classification based on only waveform features or motion data, action classification based on a combination of features such as waveform features and motion data can improve accuracy of classification.

The waveform features each include a quantity of crests, a quantity of troughs, a crest value, skewness, kurtosis, and the like. The motion data includes a jump height, a movement distance, a duration of flight, and the like. The classifier may be a logistic regression (LR) classifier, a decision tree (DT) classifier, a random forest (RF) classifier, a gradient boosting decision tree (GBDT) classifier, or the like. This is not limited in this application.

Figure 9:
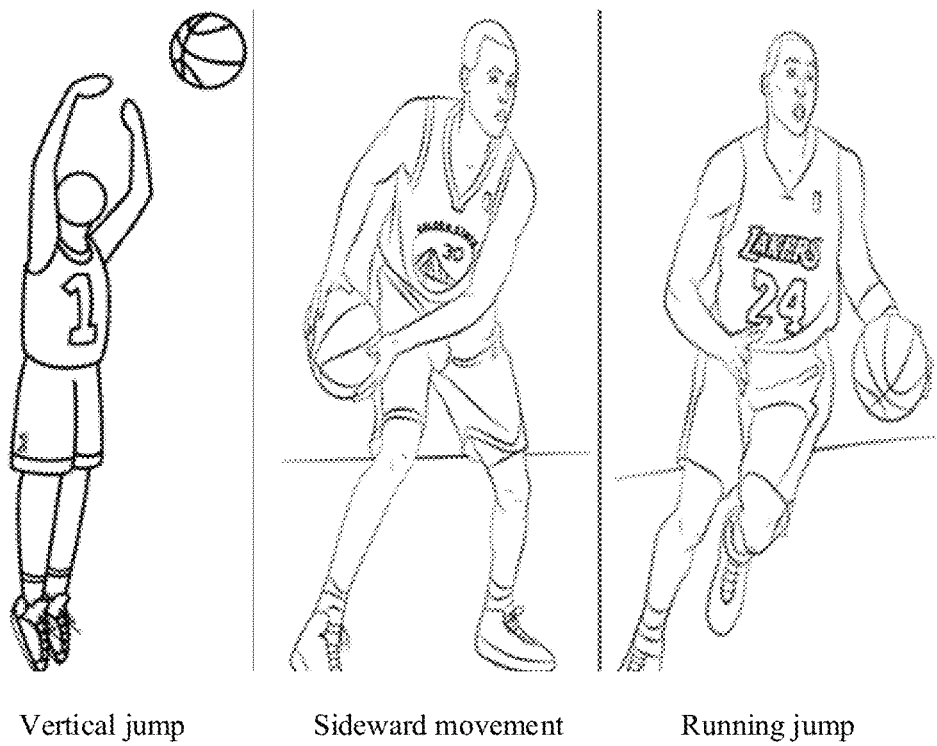
FIG. 9 is a schematic diagram of vertical jump, running jump, and sideward movement according to an embodiment of this application.

As shown in FIG. 9, basketball is used as an example. An action classification result may include perpendicular vertical jump, running jump, walking running, sideward movement, and the like, and may further include other actions. This is not limited in this application. In this way, the user can learn a clearer motion status of the user based on the action classification result, so that the user experience can be improved.

506: The electronic device performs template matching on the motion data and database data, and outputs a character classification and/or a person tag of the user.

Basketball is used as an example. The database data may include data of a plurality of users. The data of the users may include motion data (a jump height, a duration of flight, a movement velocity, and the like) of the users, user parameters (such as a height, a weight, an armspan, a shooting percentage, a liveness), an action classification result (vertical jump, running jump, and sideward movement), and the like. The data in the database may be expressed as $f_i(n)$, where i represents data of an $i^{th}$ user in the database, n=1, 2, ..., and N, and N represents a feature dimension of the data of the users (including a jump height, a duration of flight, a movement velocity, a height, a weight, an armspan, vertical jump, running jump, and the like). The database $f_i(n)$ may be normalized to obtain $F_i(n)$:

$$F_i(n) = \frac{f_i(n)}{\|f(n)\|} - (0, 1).$$

The normalization is to eliminate dimensional influence between different data indicators, so that the data indicators are in a same order of magnitude. Motion data of a current user may be expressed as $G_j(n)$, where j represents data of a $j^{th}$ round/time inputted by a current user. Optionally, $G_j(n)$ may further include an action classification result and a user parameter of the current user. The action classification result may include vertical jump, running jump, sideward movement, and the like. The external input parameter may include parameters such as a height, a weight, an armspan, and a shooting percentage of the user.

Figure 10:
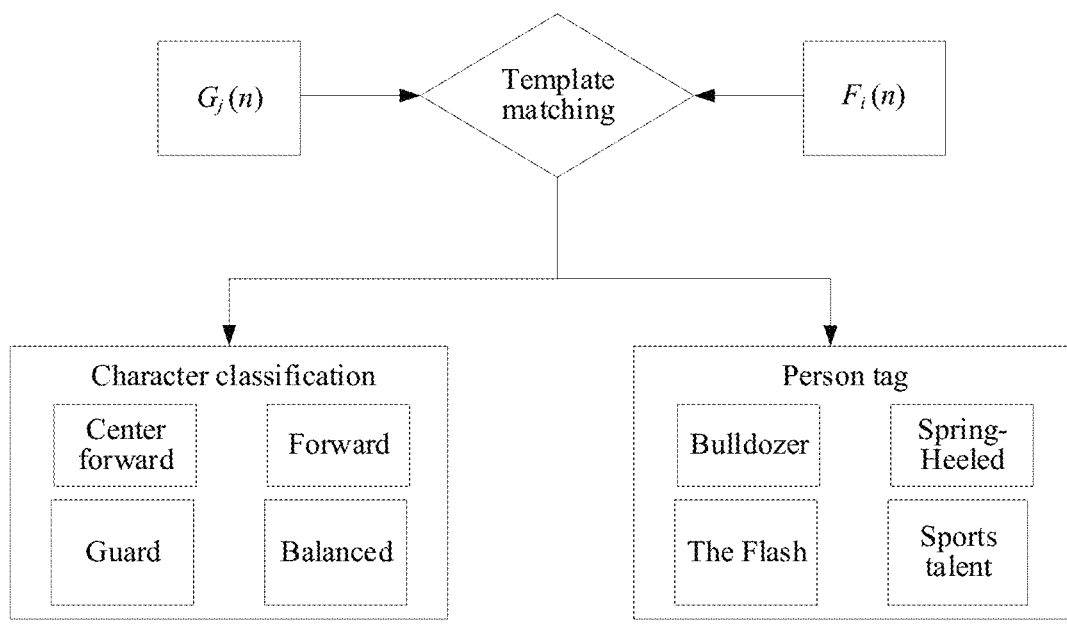
FIG. 10 is a schematic flowchart of template matching according to an embodiment of this application.

As shown in FIG. 10, the electronic device may perform template matching on $G_j(n)$ and $F_i(n)$, and output a character classification and/or a person tag of the user. For example, a matching rule may be a principle of a maximum correlation coefficient R(i, j):

$$\max\{R(i, j)\} = \max\left\{\frac{\sum_{n=1}^{n=N}(F_i(n) - \overline{F_I(N)}) * (G_j(n) - \overline{G_J(N)})}{\sqrt{\sum_{n=1}^{n=N}(F_i(n) - \overline{F_I(N)})^2 * \sum_{n=1}^{n=N}(G_j(n) - \overline{G_J(N)})^2}}\right\}.$$

After the template matching, the electronic device may output the character classification and/or the person tag of the user. For example, if a movement velocity and a vertical jump height value of the user are relatively low but a height of the user is relatively high, the character classification may be inputted as center forward. If the movement velocity and a liveness value of the user are relatively large, the character classification may be inputted as defender. In another example, if a weight of the user exceeds 80 kg and a vertical jump height exceeds 70 cm, the person tag may be inputted as Omega Supreme. If the vertical jump height exceeds 90 cm, the person tag may be inputted as a spring leg. In this way, enjoyment of sports is enhanced for the user, and the user experience can be improved.

Based on the motion data monitoring method provided in this application, the electronic device may collect the angular velocity signal and the acceleration signal of the user and process the angular velocity signal and the acceleration signal to obtain the motion data of the user. The angular velocity signal and the acceleration signal of the user may be collected by using a six-axis sensor. Costs are low and temporally synchronous transmission and data fusion for a plurality of sensor units are not required. Motion data (such as a jump height) of the user in diversified sports (for example, basketball) can be monitored in real time, and the user experience in sports can be improved.

Some other embodiments of this application further provide a motion data monitoring apparatus. The apparatus may be applied to the foregoing electronic device. The apparatus is configured to perform various functions or steps performed by the mobile phone in the foregoing method embodiments.

Figure 11:
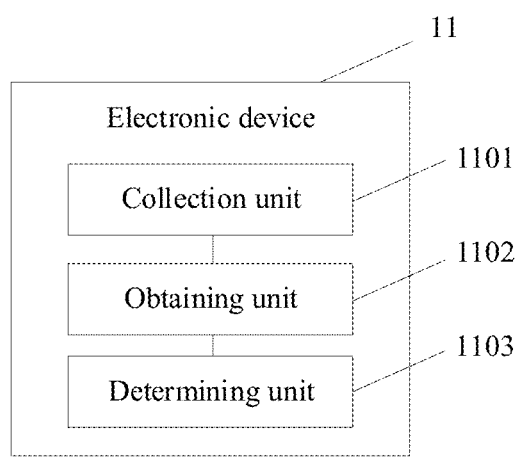
FIG. 11 is a schematic structural diagram of another electronic device according to an embodiment of this application.

In case of using functional modules corresponding to function divisions, FIG. 11 shows a possible schematic structural diagram of the electronic device in the foregoing embodiment. The electronic device is configured to implement the methods recorded in the foregoing method embodiments. The electronic device specifically includes a collection unit 1101, an obtaining unit 1102, and a determining unit 1103.

The collection unit 1101 is configured to support the electronic device to perform the process 501 shown in FIG. 5. The obtaining unit 1102 is configured to support the electronic device to perform the process 502 shown in FIG. 5. The determining unit 1103 is configured to support the electronic device to perform the processes 503-506 shown in FIG. 5. All related content of the steps in the foregoing method embodiments may be cited as functional description of the corresponding functional modules. Details are not described herein again.

An embodiment of this application further provides a computer storage medium. The computer storage medium stores computer instructions, and the computer instructions, when run on the foregoing electronic device, cause the electronic device to perform the functions or steps performed by the mobile phone in the foregoing method embodiments.

An embodiment of this application further provides a computer program product. The computer program product, when run on a computer, cause the computer to perform the functions or steps performed by the mobile phone in the foregoing method embodiments.

The foregoing descriptions about implementations allow a person skilled in the art to understand that, for the purpose of convenient and brief description, division of the foregoing functional modules is used as an example for illustration. In actual application, the foregoing functions can be allocated to different modules and implemented according to a requirement, that is, an inner structure of an apparatus is divided into different functional modules to implement all or part of the functions described above.

In the several embodiments provided in this application, it should be understood that the disclosed apparatus and method may be implemented in other manners. For example, the described apparatus embodiment is merely exemplary. For example, the module or unit division is merely logical function division and may be other division in actual implementation. For example, multiple units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electric, mechanical, or other forms.

The units described as separate parts may or may not be physically separate, and parts displayed as units may be one or more physical units, may be located in one place, or may be distributed in multiple different places. Some or all of the units may be selected according to actual requirements to achieve the objectives of the solutions of the embodiments.

In addition, functional units in the embodiments of this application may be integrated into one processing unit, or each of the units may exist alone physically, or two or more units are integrated into one unit. The integrated unit may be implemented in the form of hardware, or may be implemented in the form of a software functional unit.

If the integrated unit is implemented in the form of a software functional unit and sold or used as an independent product, the integrated unit may be stored in a readable storage medium. Based on such an understanding, the technical solutions in this embodiment of this application essentially, or the part contributing to the prior art, or all or some of the technical solutions may be implemented in the form of a software product. The software product is stored in a storage medium and includes several instructions for instructing a device (which may be a single-chip microcomputer, a chip or the like) or a processor (processor) to perform all or some of the steps of the methods described in the embodiments of this application. The foregoing storage medium includes: any medium that can store program code, such as a USB flash drive, a removable hard disk, a read-only memory (read-only memory ROM), a random access memory (random access memory, RAM), a magnetic disk, or a compact disc.

The foregoing content is merely specific implementations of this application, but are not intended to limit the protection scope of this application. Any variation or replacement within the technical scope disclosed in this application shall fall within the protection scope of this application. Therefore, the protection scope of this application shall be subject to the protection scope of the claims.

What is claimed is:

1. A motion data monitoring apparatus, comprising a processor, wherein the processor is coupled to a memory, the memory stores instructions, and the processor is configured to invoke and execute the instructions to cause the apparatus to perform:
    collecting, by an electronic device, an angular velocity signal and an acceleration signal of a user;
    obtaining, by the electronic device, a waveform feature of the angular velocity signal based on the angular velocity signal, and obtaining a waveform feature of the acceleration signal based on the acceleration signal;
    performing action classification based on the waveform feature of the angular velocity signal and the waveform feature of the acceleration signal;
    determining, by the electronic device, a gait feature of the user according to the waveform feature of the angular velocity signal and the waveform feature of the acceleration signal, wherein the waveform feature of the acceleration signal comprises two adjacent crests in a waveform of the acceleration signal, and wherein the gait feature comprises a duration of flight from off-ground of a foot of the user to touching of the ground; and
    determining, by the electronic device, motion data according to the gait feature, wherein the motion data comprises a jump height when the action classification indicates a vertical jump or running jump.

2. The motion data monitoring apparatus according to claim 1, wherein the collecting, by an electronic device, an angular velocity signal and an acceleration signal of a user comprises:
    collecting, by the electronic device, an angular velocity signal and an acceleration signal of the foot or a leg of the user.

3. The motion data monitoring apparatus according to claim 1, wherein the determining, by the electronic device, motion data according to the gait feature comprises:
    determining, by the electronic device, a first component of the jump height according to the duration of flight;
    determining, by the electronic device, a second component of the jump height according to an integration of the acceleration signal over the duration of flight; and
    determining, by the electronic device, the jump height according to the first component and the second component.

4. The motion data monitoring apparatus according to claim 3, wherein
    the determining, by the electronic device, a first component of the jump height according to the duration of flight comprises:

$$H_t = \frac{1}{2} * g \left(\frac{\Delta t}{2}\right)^2,$$

wherein $H_t$ represents the first component, $\Delta t$ represents the duration of flight, and g represents an acceleration of gravity;
    the determining, by the electronic device, a second component of the jump height according to an integration of an acceleration signal over the duration of flight comprises:
    $H_a = \iint_{t^0 + \Delta t}^{t^0} (k * acc_z) dt$, wherein $H_a$ represents the second component, $\Delta t$ represents the duration of flight, $t^0$ represents an initial moment of the duration of flight, k is a correction parameter, and $acc_z$ represents a signal component of an acceleration of the user in a z-axis direction of a local horizontal coordinate system; and
    the determining, by the electronic device, the jump height according to the first component and the second component comprises:
    when $|H_a - H_t| < \Delta H$, $H = \frac{1}{2} * (H_a + H_t)$, wherein a threshold $\Delta H$ is a preset threshold, and H is the jump height.

5. The motion data monitoring apparatus according to claim 1, wherein the determining, by the electronic device, a gait feature of the user according to the waveform feature of the angular velocity signal and the waveform feature of the acceleration signal comprises:
    determining, by the electronic device, the gait feature of the user according to the waveform feature of the angular velocity signal, the waveform feature of the acceleration signal, and an attitude angle matrix, wherein the attitude angle matrix is determined according to the angular velocity signal and the acceleration signal.

6. The motion data monitoring apparatus according to claim 5, further comprising:
    constructing, by the electronic device, an attitude angle correction matrix according to a preset condition, wherein the preset condition comprises presetting a velocity of the foot of the user before taking off from the ground to 0 and a displacement in a vertical direction to 0, and presetting a velocity of the foot of the user after touching the ground to 0 and a displacement in the vertical direction to 0; and correcting, by the electronic device, the attitude angle matrix according to the attitude angle correction matrix.

7. The motion data monitoring apparatus according to claim 6, wherein the correcting, by the electronic device, the attitude angle matrix according to the attitude angle correction matrix comprises:

$$R_c = C * R, \text{ wherein}$$

$$C = \begin{bmatrix} 1 & 0 & 0 \\ 0 & \cos\gamma & \sin\gamma \\ 0 & -\sin\gamma & \cos\gamma \end{bmatrix} \begin{bmatrix} \cos\beta & 0 & -\sin\beta \\ 0 & 1 & 0 \\ \sin\beta & 0 & \cos\beta \end{bmatrix} \begin{bmatrix} \cos\alpha & -\sin\alpha & 0 \\ \sin\alpha & \cos\alpha & 0 \\ 0 & 0 & 1 \end{bmatrix};$$

$$\gamma = \gamma_1 + \gamma_2, \gamma_1 = \arctan\left(\frac{v_z}{g\Delta t}\right), \gamma_2 = \arctan\left(\frac{H_z}{S}\right);$$

$$\beta = \arctan\left(\frac{v_y}{g\Delta t}\right); \text{ and } \alpha = \arctan\left(\frac{v_x}{g\Delta t}\right),$$

wherein

C represents the attitude angle correction matrix, R represents the attitude angle matrix, $R_c$ represents a corrected attitude angle matrix, α, β, and γ are respectively rotation angles in an x-axis direction, a y-axis direction, and the z-axis direction in the local horizontal coordinate system, $v_x$, $v_y$, and $v_z$ are respectively velocity components in the x-axis direction, the y-axis direction, and the z-axis direction, $H_z$ is a displacement in the z-axis direction, S is a displacement of the foot of the user after the taking off from the and before the touching of the ground, and Δt is a time interval from the taking off from the ground of the foot of the user to the touching of the ground.

8. The motion data monitoring apparatus according to claim 1, wherein
the motion data further comprises at least one of a movement distance, a quantity of steps, and a movement velocity of the user.

9. The motion data monitoring apparatus according to claim 1, further comprising:
performing, by the electronic device, zero-velocity correction according to a local minimum value time point of a movement velocity in a time interval from the touching of the ground to the taking off from the ground; and/or
performing, by the electronic device, distance correction according to a local minimum value time point of a displacement in the vertical direction in the time interval from the touching of the ground to the taking off from the ground.

10. The motion data monitoring apparatus according to claim 1, further comprising:
performing, by the electronic device, action classification according to the waveform feature of the angular velocity signal, the waveform feature of the acceleration signal, and the motion data, wherein an action classification result comprises at least one of vertical jump, running jump, or sideward movement.

11. The motion data monitoring apparatus according to claim 1, further comprising:
performing, by the electronic device, template matching on the motion data and database data, and outputting a character classification and/or a person tag of the user.

* * * * *